(12) United States Patent
Fagan (10) Patent No.: US 10,485,380 B2
(45) Date of Patent: Nov. 26, 2019

(54) SYSTEM AND METHOD FOR CONTROLLING OIL CONTENT IN FRIED FOOD PRODUCTS

(71) Applicant: Frito-Lay North America, Inc., Plano, TX (US)

(72) Inventor: Scott Fagan, Dallas, TX (US)

(73) Assignee: Frito-Lay North America, Inc., Plano, TX (US)

(*) Notice: Subject to any disclaimer, the term of this patent is extended or adjusted under 35 U.S.C. 154(b) by 34 days.

(21) Appl. No.: 15/793,651

(22) Filed: Oct. 25, 2017

(65) Prior Publication Data

US 2018/0110368 A1 Apr. 26, 2018

Related U.S. Application Data

(60) Provisional application No. 62/576,396, filed on Oct. 24, 2017, provisional application No. 62/413,231, filed on Oct. 26, 2016.

(51) Int. Cl.
*A47J 37/12* (2006.01)
*A23L 5/10* (2016.01)
*G01N 33/03* (2006.01)

(52) U.S. Cl.
CPC .......... *A47J 37/1214* (2013.01); *A23L 5/11* (2016.08); *A23L 5/13* (2016.08); *A23L 5/17* (2016.08); *A47J 37/1228* (2013.01); *A47J 37/1266* (2013.01); *A47J 37/1276* (2013.01); *G01N 33/03* (2013.01); *A23V 2002/00* (2013.01); *A23V 2300/10* (2013.01); *A23V 2300/24* (2013.01)

(58) Field of Classification Search
CPC ............... A47J 37/1214; A47J 37/1266; A47J 37/1276; A47J 37/1228; A23L 5/11–5/17; A23L 5/20; A23L 19/18; G01N 33/03; A23V 2002/00; A23V 2300/10; A23V 2300/24
USPC .... 426/231–233, 438–441, 523; 99/403–418
See application file for complete search history.

(56) References Cited

U.S. PATENT DOCUMENTS 2,056,845 A * 10/1936 Ferry .................. A47J 37/1214
126/376.1
3,223,024 A * 12/1965 Benson .................. A23N 12/02
99/352

(Continued)

FOREIGN PATENT DOCUMENTS

NI 8503157 A 6/1987
NL 8503157 A * 6/1987 ............. A23N 12/02

*Primary Examiner* — Drew E Becker
(74) *Attorney, Agent, or Firm* — Colin P. Cahoon; Samie S. Leigh; Carstens & Cahoon, LLP (57) ABSTRACT

A fryer system and method for producing fried food pieces are disclosed herein. A fryer, located in a frying region of the fryer system, produces fried food pieces. An adjustable draining device, located in a draining region of the fryer system, is downstream from the frying region and controls a residence time of the fried food pieces in the draining region. A set of takeout conveyors bridges the frying region and the draining region and reduces a bed depth of the fried food pieces as the set of takeout conveyors transfers the fried food pieces from the fryer to the draining device. An enclosure at least partially encloses the frying region and the draining region to maintain a controlled environment within the draining region.

19 Claims, 4 Drawing Sheets

(56) References Cited

U.S. PATENT DOCUMENTS

| | | | | |
|---|---|---|---|---|
| 4,167,137 A | * | 9/1979 | van Remmen | A21B 5/08 99/352 |
| 4,325,295 A | * | 4/1982 | Caridis | A23L 19/18 426/438 |
| 4,366,749 A | | 1/1983 | Caridis | |
| 4,379,055 A | * | 4/1983 | Carlson | A47J 37/1214 210/400 |
| 4,563,944 A | * | 1/1986 | Tate | A47J 37/1214 198/803.14 |
| 4,933,199 A | * | 6/1990 | Neel | A23L 19/18 426/438 |
| 5,167,979 A | * | 12/1992 | Benson | A47J 37/1214 426/438 |
| 5,327,708 A | * | 7/1994 | Gerrish | A01F 12/00 460/7 |
| 5,454,296 A | * | 10/1995 | Beardsley | A47J 36/38 126/299 D |
| 5,846,589 A | * | 12/1998 | Baker | A23L 5/11 426/439 |
| 5,947,010 A | * | 9/1999 | Barry | A47J 37/1271 210/DIG. 8 |
| 2006/0088633 A1 | * | 4/2006 | Barber | A23L 19/18 426/465 |
| 2009/0044706 A1 | * | 2/2009 | Foster | A47J 36/00 99/336 |
| 2010/0040750 A1 | * | 2/2010 | Assaad | A23L 5/11 426/438 |
| 2010/0112177 A1 | * | 5/2010 | Bourg, Jr. | A47J 37/1214 426/560 |
| 2011/0281005 A1 | * | 11/2011 | Desai | A23L 5/21 426/438 |
| 2012/0093991 A1 | * | 4/2012 | Schmidt | A47J 36/28 426/438 |
| 2013/0136834 A1 | * | 5/2013 | French | A47J 37/1214 426/438 |
| 2013/0251886 A1 | * | 9/2013 | Khan | A47J 37/1233 426/637 |
| 2014/0314927 A1 | * | 10/2014 | Eichenlaub | A47J 37/1214 426/438 |

\* cited by examiner

SYSTEM AND METHOD FOR CONTROLLING OIL CONTENT IN FRIED FOOD PRODUCTS

CROSS REFERENCE TO RELATED APPLICATION

This application claims the benefit of provisional U.S. Application No. 62/576,396 entitled "System and Method for Controlling Oil Content in Fried Food Products" filed Oct. 24, 2017, and provisional U.S. Application No. 62/413,231 entitled "System and Method for Fried Food Products with Reduced Oil" filed Oct. 26, 2016, the entirety of both of which are incorporated herein in their entirety.

BACKGROUND OF THE INVENTION

Technical Field

The present disclosure relates generally to a system and method for the production of a fried snack food with improved oil content control capability. More particularly, the disclosure provides for a novel, single-fryer system and a controlled draining region that allows for oil content in fried food pieces without the need for a secondary oil immersion zone.

Background

Frying food pieces causes moisture within the food piece to boil. When the food pieces are slices of raw potato, for example, boiling moisture results in disruption and delamination of cell walls that manifest as holes and voids. These holes and voids absorb frying oil during the frying process, particularly when the fried food piece begins to cool after the frying process. Excess oil can have a noticeable affect the final potato chip snack product given that oil content contributes to the overall organoleptic desirability of snack products. Too high an oil content may render the chips greasy or oily and hence less desirable to consumers. On the other hand, chips lacking a sufficient amount of oil may lack flavor and possess a harsh texture. In addition to organoleptic considerations, some nutritional guidelines suggest diets low in oil or fat.

Previous attempts to reduce the oil content in fried food products, such as potato chips, have been unsuccessful for a variety of reasons. For example, frying systems may be too expensive, or violate construction or processing limitations. Some systems may also fail to maintain the desired organoleptic properties such as taste and texture that have become familiar to consumers of traditional potato chips having higher fat or oil contents. Consequently, a need exists for a process that enables the production of a fried food product, such as a potato chip with reduced oil, but which can be produced by a fryer that satisfies certain system constraints.

SUMMARY OF THE INVENTION

In a first embodiment, the present disclosure provides for a fryer system for controlling oil content of fried food pieces. A fryer, located in a frying region of the fryer system, produces fried food pieces. An adjustable draining device, located in a draining region of the fryer system, is downstream from the frying region and controls a residence time of the fried food pieces in the draining region. A set of takeout conveyors bridges the frying region and the draining region and reduces a bed depth of the fried food pieces as the set of takeout conveyors transfers the fried food pieces from the fryer to the adjustable draining device. An enclosure at least partially encloses the frying region and the draining region to maintain a controlled environment within the draining region.

In a second embodiment, the disclosure provides for a method of producing fried food pieces in a fryer system. The method comprises frying a plurality of food pieces in hot oil to form the fried food pieces. The fried food pieces are transferred to an adjustable draining device located within a draining region of the fryer system. A controlled environment is maintained within the draining region, and the fried food pieces are conveyed through the draining region for a residence time.

Other aspects, embodiments and features of the invention will become apparent from the following detailed description of the invention when considered in conjunction with the accompanying drawings. The accompanying figures are schematic and are not intended to be drawn to scale. In the figures, each identical, or substantially similar component that is illustrated in various figures is represented by a single numeral or notation. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Novel aspects of the present disclosure relate generally to an improved fryer system and method for controlling oil content in fried food products. As an example, the novel fryer system can be used for creating fried food products having a reduced oil content. The improved fryer system addresses at least two problems associated with existing multi-stage fryer systems. First, the fryer system disclosed herein saves space by eliminating the second fryer commonly utilized in multi-fryer systems. For example, one type of multi-fryer system utilizes a second fryer with a high-temperature oil flume to reduce oil in fried food products. Space constraints may limit the ability to retrofit older, single-fryer systems with a second fryer for oil control because the legacy fryer systems may be located in crowded manufacturing facilities that lack capacity for expansion. Accordingly, novel aspects of the disclosure describe a novel draining region downstream from a fryer, which can be used for oil content control. In some embodiment, the draining region is smaller than the second fryers in multi-stage fryers, which can be more readily utilized in manufacturing facilities with space constraints. Thus, in one embodiment, the improved fryer system disclosed herein has an overall length between 13-14 meters (42.7-45.9 feet), which is about the same as that of conventional, single-fryer systems. Further, the fryer system has a frying region with a length in the range between 11-12.5 meters (36.1-41.01 feet), and a draining region with a length between 1-2 meters (3.3-6.6 feet). Restated, at least some novel aspects of the disclosure provide for a fryer system with a fryer region length and a draining region length with a ratio in the range of 5.5:1-12.5:1, which allows the fryer system to reside in a footprint of the aforementioned single-fryer systems.

Secondly, the improved fryer system decouples oil reduction from boost. Boost is a colloquial term that can be defined as "increased production capacity." Restated, some currently existing multi-fryer systems that purport to reduce oil content in fried food products also result in an unavoidable increase in production capacity. For example, some conventional multi-stage frying systems are capable of reducing oil content by as much as 25% but result in boost of around 25%. To offset any effects of undesirable boost, those fryer systems can be run at lower capacities at the expense of oil turnover rate, which results in reduced oil quality and rancid flavoring. To retrofit legacy frying systems with additional fryers to control oil content also requires further capital investment to upgrade supporting systems to accommodate the increased production and prevent bottlenecking. As an example increased production may require additional equipment for slicing, heating, and/or packing, to handle larger volume of product. In addition, increased production may require larger pieces of equipment, such as sorters and tumblers, which may not be feasible due to space constraints. Consequently the improved system and method disclosed herein recognizes the aforementioned challenges and provides a novel solution that decouples boost from oil reduction without increasing the fryer system footprint.

Figure 1:
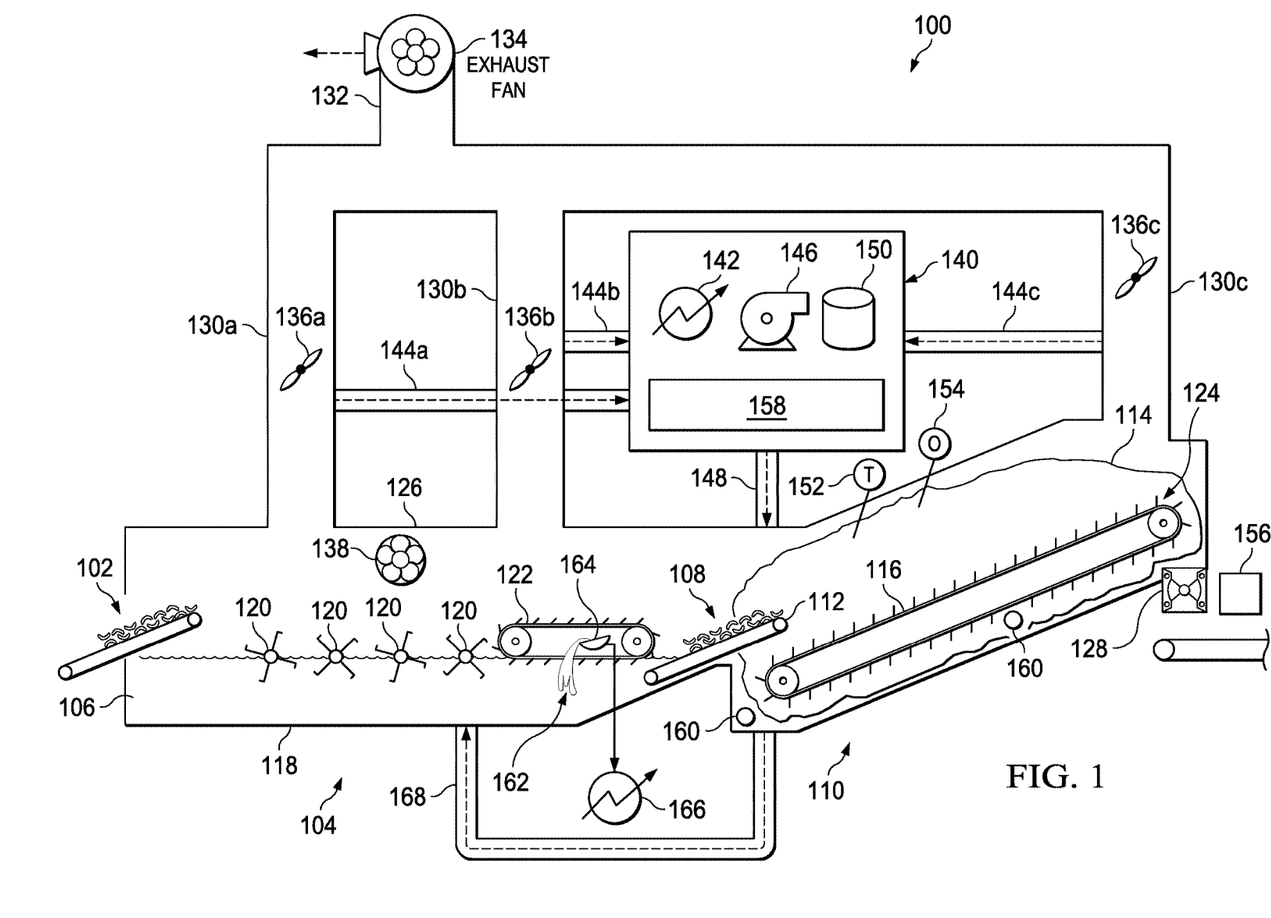
FIG. 1 is an exemplary fryer system for reducing oil content in fried food products.

FIG. 1 is a simplified diagram of an improved fryer system for controlling oil content in fried food pieces in accordance with an illustrative embodiment. The food pieces 102 discussed herein may be any type of food pieces that may be fried in preparation for consumption, such as potato slices. Food pieces 102 can also include whole or pieces of a variety of fruits and vegetables, as well as legumes, nuts and seeds. Food pieces 102 can also include fabricated chip products such as fabricated potato chips and tortilla chips. Food pieces 102 may also include extruded collets made from corn meal or other starchy ingredients, which may be direct expanded extruded products or non-expanded extruded products.

At a high level and with reference to FIG. 1, the improved fryer system 100 receives a plurality of food pieces 102 into a frying region 104 for frying in hot oil 106 to form fried food pieces 108. After frying, the fried food pieces 108 are transferred to the draining region 110 by one or more takeout conveyors 112 bridging the frying region 104 and the draining region 110. Fried food pieces 108 are conveyed through the draining region 110 to control the amount of oil in the fried food pieces 108 in accordance with the novel aspects of the present disclosure. In particular, improved oil control is achieved by maintaining a controlled environment throughout the fryer system 100, and in particular the environment within the draining region 110. The controlled environment within the draining region 110 is adjusted and/or maintained by controlling one or more of a temperature of the draining region 110, a steam concentration of the draining region 110, and an oxygen content of the draining region 110. In a non-limiting embodiment, the controlled environment in the draining region 110 is adjusted and/or maintained by a steam blanket 114.

The steam blanket 114 is a gaseous cloud that fills the volume of the draining region 110. In one embodiment, the steam blanket 114 is generated, at least in part, from steam originating from the frying of food pieces 102 in frying region 104. The steam generated during the frying of food pieces 102 may be supplemented by steam generated from another source (not shown) to adjust the amount of steam or the temperature of the steam blanket 114. Utilizing steam generated during the frying of food pieces 102 reduces the heat load requirement of the fryer system 100, which increases efficiency and operating costs. However, in another embodiment, the steam blanket 114 may include steam generated from an alternate source that does not include steam generated from the frying region 104.

The controlled environment in the draining region 110 controls oil content by affecting the reabsorption of oil by the fried food pieces 108. For example, lower temperatures in the draining region 110 decreases the viscosity of oil and decreases the vapor pressure in the voids of the fried food pieces 108, which results in increased oil content in the fried food pieces 108 by hindering oil drainage from the surface of the fried food piece 108. Conversely, higher temperatures in the draining region 110 increases the viscosity of the oil and increases the vapor pressure in the voids of the food pieces 102, which promotes oil drainage and results in a decreased oil content in the fried food pieces 108. Additionally, when the fried food pieces 108 have a generally planar configuration, such as potato chips or tortilla chips, oil reduction is further improved by maintaining the fried food pieces 108 in a vertical or generally vertical orientation in the draining region 110 by incorporating an adjustable draining device that will be described in more detail below.

Frying region 104 includes fryer 118, which can take the form of any conventional frying apparatus. In a non-limiting embodiment, the fryer 118 is a continuous single flow or multizone fryer utilizing commonly available devices such as paddle wheels 120 and a submergible conveyor belt 122 to control the flow of food pieces 102 through the hot oil 106. Additionally, the hot oil 106 may be any form of conventional frying medium, including frying mediums with digestible and/or non-digestible oils. In an example where the food pieces 102 are raw potato slices, the hot oil may be maintained at a temperature between 138-200° C. (280-390° F.). For example, one process for continuous immersion frying of potato slices uses an initial oil temperature of 171-200° C. (340-390° F.), a final oil temperature of about 138-171° C. (280-340° F.), and a residence time of about 30-300 seconds. Heated oil may be introduced into the fryer 118 at strategic locations to maintain the desired temperature profile. After frying, the fried food pieces 108 exit the hot oil 106 at the downstream end of the fryer 118.

After frying, fried food pieces 108 are removed from the hot oil 106 at a downstream end of the fryer 118 by a set of takeout conveyors 112. As used herein, the term "set" means one or more. Thus, "a set of takeout conveyors 112" can be a single takeout conveyor, or two or more takeout conveyors operating together. The set of takeout conveyors 112 transfers the fried food pieces 108 from the frying region 104 to the draining region 110 that is located adjacent to and downstream from the frying region 104. In particular, the set of takeout conveyors 112 transfers the fried food pieces 108 from the hot oil 106 in the fryer 118 onto an adjustable draining device 116 located within the draining region 110. In this illustrative embodiment of FIG. 1, adjustable draining device 116 is an inclined conveyor that supports the fried food pieces 108 as they are conveyed through the draining region 110. The adjustable draining device 116 may be inclined relative to a horizontal reference plane (not shown) to reduce the linear footprint of the draining region 110 as compared to a draining belt maintained in a horizontal orientation. As a result, residence time within the draining region 110 can be increased without increasing the length of the draining region 110 or reducing the speed of the adjustable draining device 116. However, in another embodiment the residence time of fried food pieces 108 in the draining region 110 may be adjusted by controlling any number of variables, including the rate of speed of the adjustable draining device 116 or even the number of vertical orientation devices that are ultimately utilized. In another embodiment, where space is not a limiting factor, the residence time of fried food pieces 108 in the draining region 110 can be increased by adding one or more successive draining regions 110 to the fryer system 100.

An adjustable draining device 116 may take any number of forms. In the non-limiting embodiment where the adjustable draining device 116 is an inclined conveyor, the adjustable draining device 116 be configured with a plurality of vertical orientation members 124 extending outwardly from a surface of the adjustable draining device 116. The vertical orientation members 124 can span a width of the inclined conveyor and are configured to orient the plurality of fried food pieces 108 in such a way to promote drainage of oil from the surface of the fried food piece 108 after frying. For example, where the fried food pieces 108 are potato chips that may have a generally planar form factor, the plurality of vertical orientation members 124 on the inclined conveyor are sized and spaced to prevent as many of the fried food pieces 108 as possible from achieving a horizontal or a generally horizontal orientation relative to the horizontal reference plane, which prevents oil from pooling on the upper surface of the fried food pieces 108.

In one embodiment, the vertical orientation members 124 are a plurality of fins or rod-shaped pins that span the entire width of the inclined conveyor. However the shape of the vertical orientation members 124 are exemplary and should not be deemed to be limiting.

In the depicted embodiment, the plurality of vertical orientation members 124 are angled relative to the surface of the draining belt, but maintained normally to a horizontal reference plane. However, in another embodiment, the plurality of vertical orientation members 124 may be oriented normally to the surface of the conveyor, and thus angled relative to the horizontal reference plane. In either embodiment, the plurality of vertical orientation members 124 may be oriented to cause as many of the plurality of fried food pieces 108 to achieve an orientation that is vertical or generally vertical. As used herein, the term "generally vertical" means that a majority of the fried food pieces 108 achieves an orientation that is within 20° of vertical as defined by the acceleration vector of gravity. In a more specific embodiment, the term "generally vertical" means that at least 70% of the fried food pieces 108 achieves the orientation that is within 20° of vertical. However, in another non-limiting embodiment, the fried food pieces 108 may rest on the adjustable draining device 116 at any non-zero angle relative to a horizontal reference plane. Angling the fried food pieces 108 on the adjustable draining device 116 to any degree promotes draining of oil from the surface of the fried food pieces 108, which reduces oil absorption.

Fried food pieces 108 are sometimes removed from the hot oil 106 in an agglomerated mass conventionally described as a bed of fried food pieces 108. The bed depth of the fried food pieces 108 is generally between 2.54-25.4 cm (1-10 inches), which can prevent the fried food pieces 108 from achieving a desired vertical or generally vertical orientation when they are deposited onto the adjustable draining device 116. For example, the deposition of a thick bed of fried food pieces 108 onto the adjustable draining device 116 may result in fried food pieces 108 piling up on the adjustable draining device 116 without any discernable orientation and trapping oil between the fried food pieces 108. In some embodiments, the bed depth of the fried food pieces 108 is reduced before the fried food pieces 108 are deposited onto the adjustable draining device 116. In another embodiment, the fried food pieces 108 are preferably monolayered or at least substantially monolayered before they are deposited on to the adjustable draining device 116. Qualitatively, as used herein, the term "substantially" means "very close to." Thus, a product bed that is substantially monolayered is very close to completely monolayered. As used herein, the term "substantially monolayered" can also describe food pieces traveling on a conveyor which may not be in a single layer, but which may be partially layered with an acceptable degree of overlapping pieces. For example, a substantially monolayered bed of food pieces may be used to describe a bed of food pieces that have been thinned to at least a third of the bed depth of fried food pieces 108 removed from the hot oil 106. Alternatively, a substantially monolayered bed of food pieces may describe a bed of food pieces that have been thinned to at least a quarter of the bed depth of the fried food pieces 108 removed from the hot oil 106.

Oil can be drained from monolayered fried food pieces 108 more effectively as compared to a bed of fried food pieces 108 where oil can be trapped between fried food pieces 108 that are stacked on top of one another. In addition, when the fried food pieces 108 have a planar form factor and the adjustable draining device 116 is a draining belt with a plurality of vertical orientation members 124, monolayered fried food pieces 108 are more likely to fall between adjacent vertical orientation members 124 to achieve a vertical or generally vertical orientation, rather than bridge the gap between two fins in a horizontal or substantially horizontal orientation. In one embodiment, the fried food pieces 108 may be monolayered by the set of takeout conveyors 112 before the fried food pieces 108 are transferred to the adjustable draining device 116. As discussed in more detail in FIG. 2, monolayering can be achieved by placing two or more takeout conveyors 112 in series and operating each of the takeout conveyors 112 at different speeds. In particular, the first of the set of takeout conveyors 112 that removes the fried food pieces 108 from the hot oil 106 operates at a first speed, and the second of the set of takeout conveyors 112 that deposits the fried food pieces 108 onto the adjustable draining device 116 operates at a second speed that is greater than the first speed. In this manner, the fried food pieces 108 can be monolayered, or at least substantially monolayered during the transfer from the first conveyor to the second conveyor. Additional conveyors may be added to the set of takeout conveyors 112 and placed in series downstream from the second conveyor in the event that additional processing is required to achieve a sufficiently monolayered state. In a non-limiting embodiment, the speed of the adjustable draining device 116 is operating a speed between the slowest takeout conveyor 112 and the fastest takeout conveyor 112.

As previously mentioned, the controlled environment within the fryer system 100 and in particular, within the draining region 110 can be manipulated to control oil content of fried food pieces 108. In one embodiment, the controlled environment within the fryer system 100 is preserved and/or controlled in part by completely isolating or at least substantially isolating the environment within the fryer system 100 from the external environment. In the non-limiting embodiment of FIG. 1, the environment within the fryer system 100 is isolated by enclosing the fryer system 100 with an enclosure 126. The enclosure 126 maintains heat and exhaust, which includes steam, within the fryer system 100. Thus, in the frying region 104, the enclosure 126 reduces the amount of energy required to maintain the hot oil 106 at sufficiently high temperatures for frying food pieces 102. In the draining region 110, the enclosure 126 preserves the heat and atmospheric composition favorable for oil control. In a particular embodiment where oil control of fried food pieces 108 is achieved by a steam blanket 114 that originates, at least in part from the steam generated during the frying of food pieces 102, the enclosure 126 directs the steam from the frying region 104 to the draining region 110 to form the steam blanket 114.

In this illustrative embodiment, the enclosure 126 is depicted as a single, continuous structural feature; however, in an alternate embodiment the enclosure 126 may be formed from separate enclosures that are joined together. For example, in another embodiment the enclosure 126 may be formed from a first steam hood positioned above the fryer 118 and a second steam hood positioned above the draining region 110 which are joined together to allow steam generated in the frying region 104 to travel down a length of the fryer system 100 without escaping. In some embodiments, the enclosure 126 is insulated to help maintain the temperature within the fryer system 100. In addition, the enclosure 126 may include one or more seals, such as air lock 128, to prevent the escape of heat from within the fryer system 100. Air lock 128 can be implemented in the downstream end of the draining region 110, which allows fried food pieces 108 to exit the fryer system 100 while preventing the uncontrolled escape of heat and steam from the draining region 110. Without the airlock 128, the temperature and composition of the steam blanket 114 could not be easily maintained, requiring the input of additional heat, steam, and/or inert gas to maintain the atmosphere within the draining region 110 at levels conducive to draining oil.

In some embodiments the entire enclosure 126, or at least portions of the enclosure 126 may be configured to be opened. In one non-limiting example, the portion of the enclosure 126 isolating the draining region 110 from the outside environment may be completely or partially opened to release all or part of the steam blanket 114 maintained within the draining region 110. As a result, the temperature fried food product 108 would be lowered and the viscosity of the oil on the surface of the fried food pieces 108 would be increased, increasing the oil uptake. In an alternate embodiment, to rapidly decrease a temperature within the draining region 110, a plurality of flow-control outlets extending from the portion of the enclosure 126 isolating the draining region 110 can be opened to release all or part of the steam blanket 114 to achieve the same result. Optionally, one or more blowers or fans may be switched on to increase the rate at which the steam blanket 114 is drawn out from the draining region 110. In any embodiment, the steam extracted from the draining region 110 should not be released into the plant environment around the fryer, but should instead be captured for controlled release through an exhaust conduit using conventionally available equipment.

Extending outwardly from the enclosure 126 is a set of flow-control outlets 130 for controlling the release of exhaust from selected regions of the fryer system 100. The set of flow-control outlets 130 may be positioned anywhere along the length of the fryer system 100 and in this illustrative embodiment the set of flow-control outlets includes three flow-control outlets 130a, 130b, and 130c. As can be seen, flow-control outlet 130a is positioned at an upstream location of the fryer system 100, proximate to the area in which food pieces 102 are introduced into the hot oil 106. In one embodiment, flow-control outlet 130a is located in the upstream half of the fryer 118. Flow-control outlet 130b is located downstream from flow-control outlet 130a and in this particular embodiment, flow-control outlet 130b is located in the downstream half of the fryer 118. In one embodiment, flow-control outlet 130b is located above the set of takeout conveyors 112 so that flow-control outlet 130b can be used to control the amount and composition of steam entering the draining region 110 from the downstream portion of the frying region 104. Flow-control outlet 130c is located downstream from both flow-control outlets 130a and 130b. In this illustrative embodiment, flow-control outlet 130c is located at the downstream end of the draining region 110; however, in alternate embodiments the flow-control outlet 130c may be located anywhere along the length of the enclosure 126 of the draining region 110. Although this non-limiting example of FIG. 1 includes only three flow-control outlets in the set of flow-control outlets 130, other embodiments may have more than three flow-control outlets or fewer than three flow-control outlets. In this illustrative example of FIG. 1, each of the set of flow-control outlets 130 feeds into a common exhaust conduit 132 that communicates with the exhaust fan 134. For more granular control of exhaust removal, the speed of the exhaust fan 134 can be controlled to control the rate at which exhaust may be extracted from the frying system 100. Additionally, the flow-control outlets 130 depicted in this illustrative embodiment are exhaust stacks, the flow-control outlets 130 may assume any currently existing or later developed configuration.

In a non-limiting embodiment, each of the steam flow-control outlets 130a, 130b, and 130c includes a corresponding damper 136a, 136b, and 136c, which are adjustable plates configured to control flowrate through their respective flow-control outlet. Specifically, each damper 136a, 136b, and 136c can be manipulated to achieve a completely open orientation, a partially opened orientation, or a completely closed orientation. By controlling the orientation of each of the dampers 136a, 136b, and 136c, the release of exhaust, from particular regions within the frying system 100 can be controlled, which in turn controls the amount of steam and temperature of steam that enters the draining region 110 to form the steam blanket 114. For example, knowing that a greater amount of steam is generated in the upstream half of the frying region 104, the selective opening and closing of dampers 136 can be used to control the amount, temperature, and/or composition of the steam blanket 114. In one illustrative example, opening the damper 136a of flow-control outlet 130a reduces the amount of steam and temperature of the resultant steam blanket 114. Conversely, closing the damper 136a of the flow-control outlet 130a increases the amount of steam and the temperature of the steam blanket 114. Likewise, dampers 136b and 136c may also be adjusted for more granular control of the temperature and composition of the steam blanket 114. The fryer system 100 may also include a set of fans or blowers 138 to control the flowrate of exhaust from the frying region 104 to the draining region 110 to form the steam blanket 114. The exhaust includes steam, which is used to form the steam blanket 114.

The atmospheric conditions within the draining region 110 are controlled, at least in part, by controlling the amount, composition, and temperature of superheated steam introduced into the draining region 110 to form the steam blanket 114. In some embodiments, the amount, composition, and temperature of the superheated steam in the draining region 110 is controlled by opening and closing one or more dampers 136. In addition or in the alternative, the amount, temperature, and composition of the steam blanket 114 may also be modified by environmental control subsystem 140. The environmental control subsystem 140 is a system that includes any conventionally available hardware and/or software to actively adjust and/or maintain system variables to achieve the controlled environment within the draining region 110. For example, the exemplary environmental control subsystem 140 of FIG. 1 includes a set of feed lines 144 in fluid communication with a return line 148, a heat exchanger 142, and an inert gas dispenser 150.

In one embodiment, the environmental control subsystem 140 maintains a temperature of the controlled environment within the draining region 110 by forming or supplementing a steam blanket 114 from exhaust generated during the frying of food pieces 102 in fryer 118, optionally heating the exhaust with a heat exchanger 142, then injecting the heated exhaust into the draining region 110. With reference to FIG. 1, environmental control subsystem 140 may generate a steam blanket 114 from exhaust captured from either the frying region 104, the draining region 110, or both. In particular, the steam may be captured by one or more feed lines 144 connected to unique locations along a length of the fryer system 100, optionally re-heated by the heat exchanger 142, and introduced into the draining region 110 by the return line 148. In this illustrative embodiment in FIG. 1, fryer system 100 includes three feed lines 144a, 144b, and 144c originating from one of the flow-control outlets 130a, 130b, and 130c, respectively. In this manner, exhaust exiting from the fryer system 100 through one of the set of flow-control outlets can be recaptured and fed back into the draining region 110 to control the temperature and composition of the steam blanket 114. Although the set of feed lines 144 are shown as extending from flow-control outlets 130a, 130b, and 130c and into the environmental control subsystem 140, in alternate embodiments the feed lines 144 may have inlets positioned anywhere along length of the frying region 104 and the draining region 110 depending upon the particular embodiment, originating from either a position on a flow-control outlet or along the length of the enclosure 126.

By controlling the location from which exhaust is drawn, characteristics of the steam blanket 114 may be controlled. For example, the difference in temperature of the steam drawn from the frying region 104 and the draining region 110 can be used to control the temperature of the steam blanket 114. For example, steam generated at the upstream end of the frying region 104 is more abundant and hotter than steam captured downstream. Thus, if the temperature of the steam blanket 114 is too high, the steam blanket 114 can include a greater proportion of cooler steam captured from the downstream end of the draining region 110 to lower the temperature of the steam blanket 114. This effect can be achieved by opening damper 136a to allow the hotter steam to escape from the upstream flow-control outlet 130a. Alternatively, if the temperature of the steam blanket 114 is too low, then a greater proportion of steam from the frying region 104 may be used to form the steam blanket 114. Although the heat drawn from the frying region 104 may also require re-heating, its relatively higher temperature as compared to the steam drawn from the draining region 110 requires less energy to re-heat and may be preferable in some embodiments.

In another example illustrating the effect of steam location on the characteristics of the steam blanket 114, a steam blanket 114 that has a higher concentration of steam has a higher thermal conductivity and higher heat capacity, which enables the fried food pieces 108 to attain hotter temperatures while residing on the adjustable draining device 116. Hotter temperatures results in less viscous oil that drains more readily from the surface of fried food pieces 108. Moreover, higher steam concentrations reduces the oxygen content of the steam blanket 114, which has the effect of slowing the rate of oil oxidation. Higher concentrations of steam can be drawn from locations along the length of the frying region 104 to increase oil reduction, or higher concentrations of steam can be drawn from locations along the length of the draining region 110 to increase oil absorption.

In other embodiments, recaptured steam drawn from a flow-control outlet 130 located further downstream is preferable so that negative pressure conditions are avoided, which could detrimentally reduce or prevent the flow of steam throughout the fryer system 100. In the event that steam drawn from an upstream end of the frying region 104 is preferable for increasing the temperature of the steam blanket 114, the strategic placement of one or more fans 138 at various locations may offset negative pressure conditions. Additional equipment may also be used in conjunction with the set of fans 138 to facilitate the movement of steam through the fryer system 100, such as a flow meter (not shown).

Although the exemplary embodiment in FIG. 1 depicts a steam blanket 114 formed from steam captured from various locations along a length of the fryer system 100, in another embodiment, the steam blanket 114 can be supplemented by steam originating from an external source (not shown). Alternatively, the steam blanket 114 can be provided entirely by the external source.

The environmental control subsystem 140 may also include one or more pumps or blowers 146 to facilitate the extraction/capture of steam from the various locations along the length of the fryer system 100. The environmental control subsystem 140 may also include an inert gas dispenser 150 configured to inject an inert gas, such as nitrogen, into the draining region 110. The inert gas may be used to displace oxygen in the steam blanket 114 so that predetermined oxygen levels may be achieved. Control of the oxygen content is desirable to reduce the rate of oil oxidation, which preserves the longevity of the cooking oil and prevents the fried food pieces 108 from developing undesirable tastes. In a non-limiting embodiment, the steam blanket 114 should provide a steam environment that is at least 80% steam, or in a more preferred embodiment, at least 90% steam with an oxygen level that is below 10%, or more preferably below 5%, such as an oxygen level that is below 2%. Additionally, where the fried food pieces 108 are potato chips, the predetermined temperature of the steam blanket 114 should be in the range of 150-190° C. (302-374° F.), more preferably between 165-175° C. (329-347° F.).

Although the environmental control subsystem 140 is shown in FIG. 1 is depicted as located above the fryer 118 and above the adjustable draining device 116, in an alternate embodiment components of the environmental control subsystem 140 may be found at a height below the pan of fryer 118 to facilitate the cleaning of those components. For example, in one embodiment, the heat exchanger 142 and the pump 146 may be located at a height below the pan of fryer 118 so that gravity can assist the transfer of cleaning solution from the fryer 118 to the heat exchanger 142 and the pump 146.

A feedback system may be implemented within the fryer system 100 to control an amount of oil on fried food pieces 108. In the illustrative embodiments disclosed herein, the feedback system may include any conventional software and/or hardware components, including but not limited to feedback control unit 158, wired and/or wireless communications lines (omitted for simplicity), and sensors, such as oil content sensor 156. Feedback control unit 158 is a software-based control unit with associated hardware components configured to automatically adjust fryer system variables to achieve a preferred oil content in fried food pieces 108 if the oil content falls outside of a preferred oil content range. Thus, in one embodiment, the feedback control unit 158 receives oil content data from an oil content sensor 156 located downstream from the draining region 110. The oil content sensor 156 may determine the final oil content of the fried food pieces 108 using conventional means, such as infrared spectroscopy. Once captured, the oil content data may be transmitted to the feedback control unit 158 to adjust fryer system variables to achieve an oil content that falls within a predetermined range. In particular, fryer system variables relevant to oil control include system settings and operational setpoints that may affect residence time of fried food pieces 108 in the draining region 110, the temperature of the steam blanket 114, composition of the steam blanket 114, temperature of the hot oil 106, and those fryer variables that affect oil content.

For example, fryer system variables that affect oil content may include any modifiable setting including but not limited to the speed of system components, such as paddle wheels 120, submergible conveyor 122, set of takeout conveyors 112, and adjustable draining device 116, which affect residence times in the frying region 104 and the draining region 110. Additionally, fryer system variables may also include the orientation of the set of dampers 136, which may be used to control not only the amount of steam that is released from the fryer system 100, but also the location from which steam is released. Selective release of steam may be used to control the temperature and composition of the steam blanket 114 in the draining region 110 as previously discussed.

In one embodiment, fryer system variables may also be automatically adjusted in the absence of oil content data from oil content sensor 156. For example, the draining region 110 may have a temperature setpoint monitored by a temperature sensor 152. Steam temperature data captured by temperature sensor 152 and transmitted to feedback control unit 158 may be used to adjust the amount and temperature of the steam introduced into the draining region 110 to maintain a temperature that facilitates draining of oil. Likewise, the draining region 110 may include an oxygen sensor 154 that monitors oxygen content. Oxygen data captured by oxygen sensor 154 can be transmitted to feedback control unit 158 to adjust an amount of inert gas introduced into the draining region to control oxygen content.

Fryer system variables may also include the speed settings for the exhaust fan 134, set of fans 138, and pump 146 to control the rate at which gasses are conveyed throughout the fryer system 100. Other fryer system variables include temperature setpoints for heat exchangers, such as heat exchanger 142, or a temperature setpoint in the draining region 110. Increasing or decreasing the temperature settings of heat exchanger 142 has an obvious effect on changing the temperature of the steam blanket 114.

Further, in the embodiment where environmental control subsystem 140 includes multiple feed lines, such as feed lines 144a, 144b, and 144c, fryer system variables may include the identity of the one or more feed lines from which steam is drawn into the environmental control subsystem 140, and the flow rate of steam through the one or more feed lines 144. For example, the feedback control unit 158 may selectively open and close control valves (not shown) positioned along feed lines 144 to control which feed line(s) 144 supply the environmental control subsystem 140 with steam, and also the flow rate of the steam. The feedback control unit 158 may adapt heat input into the steam blanket 114 being circulated through the environment control subsystem 140 controlling to a target environment temperature and/or composition once as it is injected into the draining region 110 via return line 148. In addition, the feedback control unit 158 may increase the flow rate of the inert gas injected into the draining region 110 in the event that oxygen levels are too high. Alternatively, the feedback control unit 158 may display relevant information on a user interface (not shown) to notify an operator when system variables require adjustment in order to maintain a temperature and/or composition of the steam blanket 114. The operator may then manually adjust system variables to achieve the proper oil content in the fried food pieces 108.

The feedback system may also be used to control the composition of a steam blanket 114 in the draining region 110. Accordingly, another fryer system variable may include the flow rate of inert gasses from an inert gas dispenser 150. As previously mentioned, the flowrate of inert gasses may be used to control the composition of the steam blanket 114 by displacing oxygen. The feedback control unit 158 may automatically increase or decrease the amount of inert gas introduced into the draining region 110 based on steam composition data captured by the oxygen sensor.

The fried food pieces 108 drain on the adjustable draining device 116 for a residence time. In one embodiment, the residence time is between 3-60 seconds; however, in other embodiments the residence time can be 3-25 seconds, or between 3-15 seconds. Thereafter, the fried food pieces 108 are dropped through air lock 128 for further processing. As an example, the further processing may include packaging, or the processing may include a seasoning step prior to packaging, or a post-fry dehydration step. Some shelf-stable snack foods are dehydrated to a moisture content below about 5% by weight. In one embodiment, the food pieces 102 described above exiting the air lock 128 have a moisture content about 2% by weight, and then subjected to a drying step that dehydrates the food pieces 102 to a moisture content below about 2% by weight, or below about 1.5% by weight. In various embodiments, the drying step can be one or a combination of hot air drying, microwave drying, infrared drying, or impingement drying. Other non-frying drying methods which are known in the art can be used.

Fryer system 100 may also include one or more oil flush ports 160 dispersed through the fryer system 100 for preventing the buildup of fried food pieces 108 that may result during the frying process. The one or more oil flush ports 160 are spraying devices coupled to a source of hot oil and positioned so that the oil flush ports 160 can spray hot oil at locations where buildup of fried food pieces 108 has been observed or is likely. The hot oil may be drawn from the fryer 118 or an independent source (not shown). In one embodiment, the one or more oil flush ports 160 may be located at either end of the adjustable draining device 116, which has been observed as locations where fried food pieces 108 tend to aggregate.

Aspects of the novel frying system 100 described in FIG. 1 decouples oil control from boost to address certain scenarios where the frying system 100 is incapable of accommodating increased production capacity. However, in the event that increased production capacity is desirable and can be accommodated, the frying system 100 can be configured to include a hot oil finish frying step at the downstream end of the fryer 118. The hot oil finish frying step subjects the fried food pieces 108 to oil at a temperature between 300-380° F. (149-193° C.). The higher temperature improves the heat transfer that hastens the cooking of the fried food pieces 108 which provides for a shorter dwell time in the fryer 118. Additionally, the fried food pieces 108 removed from the fryer 118 are coated with oil having a higher temperature and lower viscosity, which would reduce the dwell time of the fried food pieces 108 in the draining region 110 because the hotter oil drains quicker from the surface of the fried food pieces 108. Reduced dwell times in the frying region 104 and the draining region 110 yield an increase in production capacity, which could provide boost without increasing a footprint of the fryer system 100.

In one embodiment, the hot oil finish frying step is achieved by way of a set of one or more hot oil curtains that cascades down onto a product bed passing under submergible conveyor belt 122. The hot oil curtain may be provided by oil dispenser 164, which may be in the form of a conventionally available equipment, such as a nozzle or an outlet from an oil line. In another embodiment, the oil dispenser may be a hot oil weir system implemented as a series one or more parallel troughs suspended across a width of the fryer 118, or alternatively as an oil dispensing manifold suspended across a width of the fryer 118. In the embodiment depicted in FIG. 1, the hot oil finish frying capability is provided by one or more hot oil curtains 162 from a hot oil dispenser 164 located within a volume bounded by the upper and lower conveying surfaces of the submergible conveyor belt 122 or in the volume of space located above the submergible conveyor belt 122.

In still another embodiment, the fried food pieces 108 can be subjected to a hot oil finish frying step by a submerged hot oil curtain 162 inside the hot oil 106. In either embodiment, oil used for the hot oil finish frying step can be recycled in whole or in part from the fryer 118, or may be supplemented or replaced by a source of fresh oil (not shown). Regardless of source, the oil is heated by a heat exchanger 142 before introduction back into the frying region 104 as a hot oil curtain 162.

Draining region 110 may include an optional oil recirculation line 168 that removes oil collected from within the draining region 110. The oil may originate from the oil flush ports 160 that spray hot oil to dislodge fried food pieces 108 that may build up over time, or the oil may drain from the fried food pieces 108 as they are conveyed along the adjustable draining device 116. In this illustrative embodiment, the hot oil is fed back into the fryer 118 for use in maintaining the amount of hot oil 106. Although not shown, the oil recirculation line 168 may feed oil into the fryer oil recirculation system and ultimately the fryer heat exchanger, such as heat exchanger 166 for reheating before reinjecting the oil into the fryer 118. In another embodiment, the oil recirculation line 168 may be routed to an oil treatment system and discarded.

Figure 2:
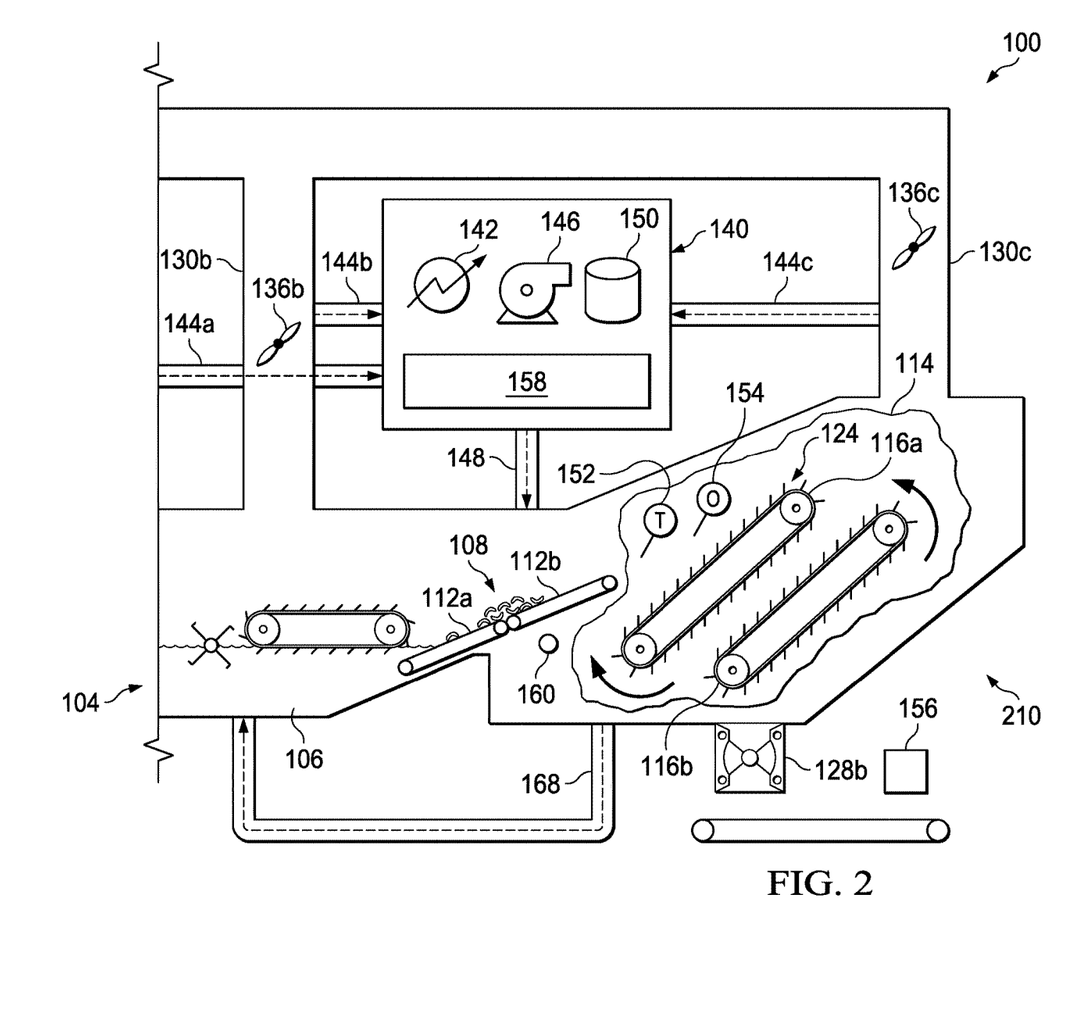
FIG. 2 is an alternate embodiment of a draining region of a fryer system for reducing oil content in fried food products.

FIG. 2 depicts an alternate configuration for a draining region for controlling oil content in accordance with another illustrative embodiment. Thus, draining region 210 from FIG. 2 may be used to replace the draining region 110 from FIG. 1.

Draining region 210 receives fried food pieces 108 from a set of takeout conveyors 112 that bridges the frying region 104 and draining region 210. In this example, the set of takeout conveyors 112 includes two takeout conveyors 112a and 112b. The first takeout conveyor 112a removes fried food pieces 108 from the hot oil 106 while operating at a first speed. The fried food pieces 108 are transferred from the first takeout conveyor 112a to the second takeout conveyor 112b which operates at a speed that is faster than the first speed. In this manner, a plurality of fried food pieces 108 removed from the hot oil 106 as a bed of product can be monolayered or at least substantially monolayered before they are deposited onto the adjustable draining device 116. Additional conveyors may be placed in series downstream from the second takeout conveyor 112b and configured to rotate at a higher speed than the immediately preceding takeout conveyor 112a to further process the fried food pieces 108 to attain a monolayered or substantially monolayered arrangement.

The set of takeout conveyors 112 transfers fried food pieces 108 to an adjustable draining device 116, which is configured as a set of inclined draining belts in this illustrative embodiment. The set of inclined draining belts 116 includes a first, upper adjustable draining device 116a located above a second, lower adjustable draining device 116b. The lower adjustable draining device 116b is positioned below the upper adjustable draining device 116a and is configured to rotate in an opposite direction from the upper adjustable draining device 116a. Thus, in this illustrative embodiment, the upper adjustable draining device 116a rotates in the clockwise direction and the lower adjustable draining device 116b rotates in a counterclockwise direction. Consequently fried food pieces 108 deposited onto the upstream end of the upper adjustable draining device 116a travel in an inclined path toward the downstream end of the fryer system 100 are eventually deposited onto the upstream end of the lower adjustable draining device 116b. Thereafter, the fried food pieces 108 are conveyed along a declined path in a direction toward the upstream end of the fryer system 100. In this illustrative embodiment, the vertical orientation device is a plurality of draining belts mounted in a stacked configuration. By stacking two draining belts, a residence time in the draining region 210 may be increased without increasing the footprint of the draining region 210. Although only two draining belts are depicted in the set of draining belts, three or more draining belts may be similarly stacked to further increase the residence time within the draining region 210. In this illustrative embodiment, fryer system variables may be adjusted to further control the residence time within the draining region 210. For example, the speed at which the adjustable draining device 116 operates may be adjusted to increase or decrease residence time. Additionally, the number of draining belts may be a fryer system variable that may be adjusted to achieve a desired residence time. For example, to reduce the residence time of fried food pieces 108 traveling through draining region 210, the draining belt 116b may be withdrawn so that fried food pieces 108 reaching the end of the draining belt 116a may be dropped directly through the air lock 128b rather than onto the draining belt 116b.

Although FIG. 2 has been depicted without an oil dispenser for introducing a hot oil curtain to the fryer 118, in an alternate embodiment an oil dispenser may be implemented at the downstream end of the frying region 104, immediately before the set of takeout conveyors 112 to increase the finish fry temperature of the fried food pieces 108 prior to extraction from hot oil 106.

Figure 3:
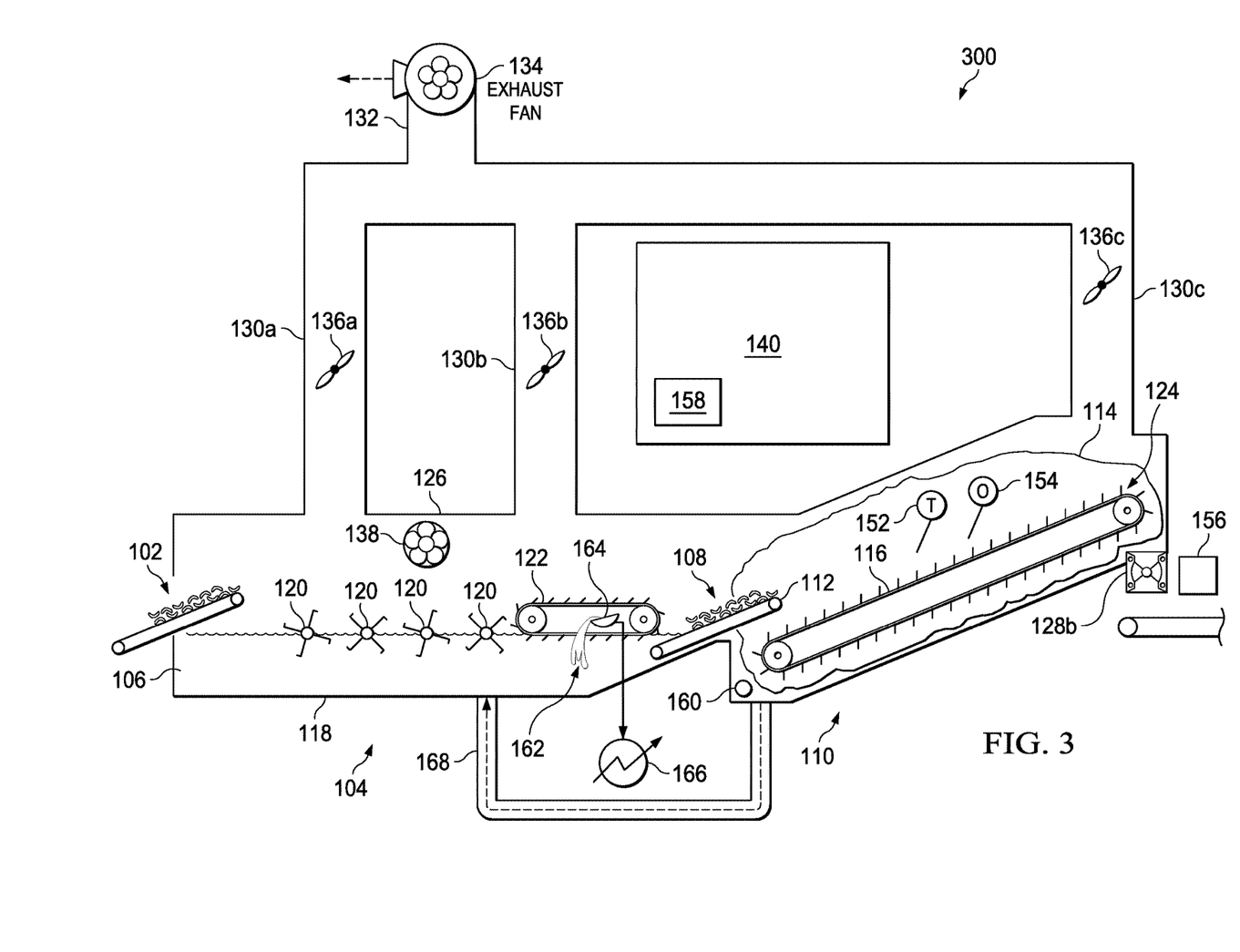
FIG. 3 is a fryer system for reducing oil content in fried food products in accordance with another illustrative embodiment.

FIG. 3 is an improved fryer system in accordance with another illustrative embodiment. The fryer system 300 is configured to receive a plurality of food pieces 102 into the frying region 104 for frying in hot oil 106 to form the fried food pieces 108. After frying, the fried food pieces 108 are transferred to the draining region 110 by a set of takeout conveyors 112 bridging the frying region 104 and the draining region 110. Specifically, the set of takeout conveyors 112 remove the fried food pieces 108 from the hot oil 106 in the fryer 118 and transfer the fried food pieces 108 onto the adjustable draining device 116.

In this illustrative embodiment in FIG. 3, the draining region 110 is located downstream from the frying region 104 and is maintained at a predetermined temperature by a steam blanket 114 formed wholly from steam generated from the frying region 104. The steam is maintained within the fryer system 300 by an enclosure 126 that encloses the frying region 104 and the draining region 110 to form a contiguous volume of space. The temperature and composition of the steam blanket 114 maintained within the draining region 110 is controlled, at least in part, by a set of damper-controlled steam flow-control outlets 130 extending outwardly from the enclosure 126 and positioned along a length of the fryer system 300, which permits the selective release of exhaust from within the fryer system 300.

Each of the set of flow-control outlets 130a, 130b, and 130c feeds into a common exhaust conduit 132 that communicates with the exhaust fan 134. Additionally, each of the damper-controlled steam flow-control outlets 130a, 130b, and 130c includes a corresponding adjustable damper 136a, 136b, and 136c. As already mentioned, each damper 136a, 136b, and 136c can be manipulated to achieve a completely open orientation, a partially opened orientation, or a completely closed orientation. By controlling the orientation of each of the dampers 136a, 136b, and 136c, the release of steam from the frying system 300 can be controlled, which in turn controls the amount of steam and temperature of steam that enters the draining region 110 to form the steam blanket 114. For example, knowing that a greater amount of steam is generated in the upstream half of the frying region 104, the selective opening and closing of dampers 136a, 136b, and 136c can be used to control an amount and/or a composition of steam in the steam blanket 114. In one illustrative example, opening the damper 136a of steam flow-control outlet 130a reduces the amount of steam and temperature of the resultant steam blanket 114. Conversely, closing the damper 136a of the steam flow-control outlet 130a increases the amount of steam and the temperature of the steam blanket 114. Likewise, dampers 136b and 136c can also be adjusted for more granular control of the temperature and composition of the steam blanket 114. Furthermore, although the flow-control outlets 130 are depicted as controlled by adjustable dampers 136, any form of conventional flow control system may be utilized instead.

In the illustrative embodiment in FIG. 3, the fryer system 300 also includes a feedback control unit 158 tasked with maintaining the proper temperature and/or composition of the steam blanket 114 within the draining region 110 in the manner previously described, but without the assistance of an environmental control subsystem 140. Thus, the fryer system 300 maintains the controlled environment in the draining region 100, and in particular the characteristics of the steam blanket 114 by adjusting the orientation of one or more dampers 136 to determine the source(s) and/or amount(s) of steam forming the steam blanket 114. Additional fryer system variables may include, for example, speed settings for the exhaust fan 134 and the set of fans 138 to control the rate at which gasses are conveyed throughout the fryer system 300.

As previously mentioned, fryer system variables may be adjusted in view of oil content data captured by oil content sensor 156, or based on data captured by temperature sensor 152, and/or oxygen content sensor 154. Restated, the fryer system variables may be adjusted if the feedback control unit 158 determines that the desired oil content level is unacceptable, or if fryer system setpoints (e.g., temperature setpoints or oxygen content setpoints) are violated.

Although the exemplary fryer system 300 in FIG. 3 is depicted with a single exhaust conduit 132, in another embodiment two or more exhaust conduits may be utilized. Further, the fryer system 300 of FIG. 3 is shown without an external steam source; however, in an alternate embodiment, the steam captured from the fryer system 300 can be supplemented by steam generated by an external steam source (not shown).

Figure 4:
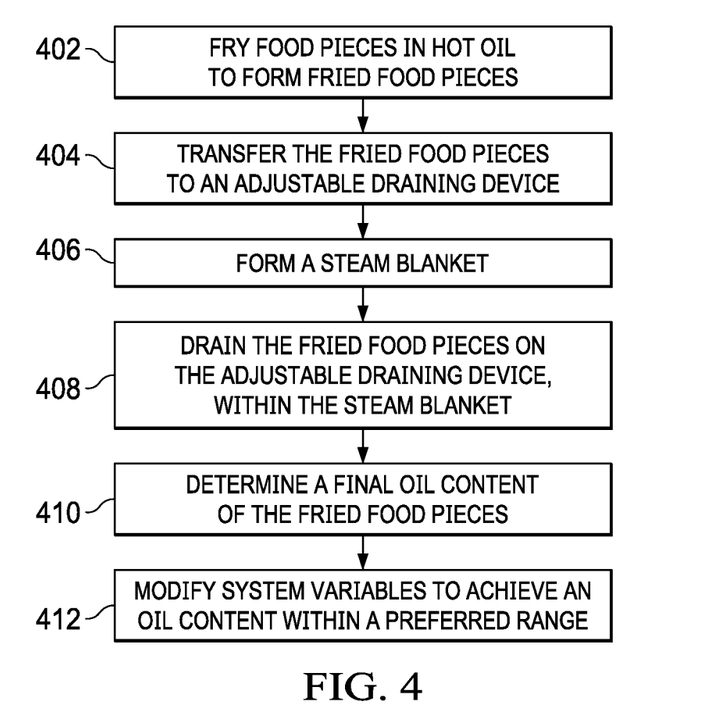
FIG. 4 is a method for creating fried food products with reduced oil content in accordance with an illustrative embodiment.

FIG. 4 is a flowchart of a method for producing fried food pieces with reduced oil content in accordance with an illustrative embodiment. Steps of the method may be implemented in an improved fryer system, such as fryer system 100 in FIG. 1. In a first step, a plurality of food pieces is fried in hot oil to form a plurality of fried food pieces (Step 402).

Thereafter, the plurality of fried food pieces are transferred to an adjustable draining device (Step 404). In one embodiment, the transferring step is performed by a set of takeout conveyors that reduces a bed depth of the fried food pieces that are removed from the hot oil. In a particular embodiment, the set of takeout conveyors reduces the bed depth to substantially monolayered or entirely monolayered. The fried food pieces may then be deposited onto the draining belt.

A steam blanket is formed that envelops the adjustable draining device (Step 406). In one embodiment, the steam blanket is formed from steam drawn from either the frying region, the draining region, or both, and optionally reheated before the steam is injected into an upstream end of the draining region to form the steam blanket. In another embodiment, the steam blanket is formed by controlling the amount of steam that can escape from one or more of a plurality of stacks placed throughout the fryer system. In another embodiment, the steam is formed entirely from an external steam source, or from steam generated in part from the frying step but supplemented with steam originating from an external steam source. Regardless of how the steam blanket is formed, the predetermined temperature of the steam blanket is in the range of 105-180° C. (221-356° F.).

The plurality of food pieces on the draining belt are drained within the steam blanket (Step 408). In one embodiment, the dwell time on the draining belt is between 3-60 seconds, between 3-25 seconds, and more preferably between 3-15 seconds. In some embodiments, where the fryer system includes a feedback system as described above, the method may include the optional steps of determining a final oil content of the fried food pieces (Step 410), and if the final oil content is not within the preferred range, then system variables are modified to achieve a final oil content within the preferred range (Step 412).

The system and method disclosed herein have several notable advantages over the prior art, particularly multi-stage fryers. First, oil reduction is decoupled from boost. Restated, fried food pieces with reduced oil content can be attained without a concomitant increase in production capacity. Preliminary tests show that the oil reduction in fried potato chips is at least 15% and the production capacity is about 6500 pounds per hour, which is on par with traditional immersion fryer systems. As previously mentioned, decoupling oil reduction from boost reduces the capital expenses necessary to retrofit existing systems with oil reduction technology. To the extent that increased production capacity can be accommodated, the fryer system may include a hot oil curtain at the downstream end of the frying region to reduce the dwell time in the fryer. In addition, the improved fryer system disclosed herein accomplishes oil reduction in a spatially efficient design, which is critical for pre-existing production lines that have limited space for expansion. Specifically, replacing the second fryer of existing thermobaric fryers with a draining region as described above reduces the overall length of the fryer system by about 5 meters, which is particularly relevant when attempting to reconfigure legacy frying systems to provide oil reduction capabilities. Lastly, the single fryer system uses less oil than other double-fryer systems, meaning there is a lower risk for oil quality issues because oil turnover rate is higher due to the lower oil volume. This is of particular value when running reduced oil product because chips also carry less oil out with them, further reducing oil turnover.

Although embodiments of the invention have been described with reference to several elements, any element described in the embodiments described herein are exemplary and substituted, added, combined, or rearranged as applicable to form new embodiments. A skilled person, upon reading the present specification, would recognize that such additional embodiments are effectively disclosed herein. For example, where this disclosure describes characteristics, structure, size, shape, arrangement, or composition for an element or process for making or using an element or combination of elements, the characteristics, structure, size, shape, arrangement, or composition can also be incorporated into any other element or combination of elements, or process for making or using an element or combination of elements described herein to provide additional embodiments. For example, it should be understood that the method steps described herein are exemplary, and upon reading the present disclosure, a skilled person would understand that one or more method steps described herein can be combined, re-ordered, or substituted.

Additionally, where an embodiment is described herein as comprising some element or group of elements, additional embodiments can consist essentially of or consist of the element or group of elements. Also, although the open-ended term "comprises" is generally used herein, additional embodiments can be formed by substituting the terms "consisting essentially of" or "consisting of."

While this invention has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Additional Embodiments

The following descriptive embodiments are offered in further support of the disclosed invention.

In a first embodiment, novel aspects of the present disclosure are directed to a fryer system comprising: a fryer in a frying region of the fryer system, wherein the fryer produces fried food pieces; an adjustable draining device in a draining region of the fryer system, wherein the draining region is downstream from the frying region, and wherein the adjustable draining device controls a residence time of the fried food pieces in the draining region; a set of takeout conveyors bridging the frying region and the draining region, wherein the set of takeout conveyors reduces a bed depth of the fried food pieces as the set of takeout conveyors transfers the fried food pieces from the fryer to the draining device; and an enclosure at least partially enclosing the frying region and the draining region, wherein the enclosure maintains a controlled environment within the draining region.

In another aspect of the first embodiment, the fryer system comprises: a fryer in a frying region of the fryer system, wherein the fryer produces fried food pieces; an adjustable draining device in a draining region of the fryer system, wherein the draining region is downstream from the frying region, and wherein the adjustable draining device controls a residence time of the fried food pieces in the draining region; a set of takeout conveyors bridging the frying region and the draining region, wherein the set of takeout conveyors reduces a bed depth of the fried food pieces as the set of takeout conveyors transfers the fried food pieces from the fryer to the draining device; and an enclosure at least partially enclosing the frying region and the draining region, wherein the enclosure maintains a controlled environment within the draining region; and one or more feature selected from the following:

wherein the adjustable draining device is a vertical orientation device that orients the fried food pieces in at least a generally vertical orientation;

wherein the adjustable draining device is set of conveyor belts, wherein each of the set of conveyor belts comprises a plurality of vertical orientation members extending outwardly from a conveying surface, and wherein the plurality of vertical orientation members span a width of the conveyor;

wherein the adjustable draining device comprises at least one of a variable velocity, a variable elevation, and a variable number of conveyor belts in the set of conveyor belts;

wherein the set of takeout conveyors comprises a plurality of conveyor belts arranged in series, and wherein the set of takeout conveyors reduces the bed depth of the fried food pieces to a substantially monolayered state;

wherein each downstream conveyor belt in the plurality of conveyor belts has a higher velocity than an upstream conveyor belt;

wherein the set of takeout conveyors comprises at least two conveyors arranged in series, wherein a first conveyor removes fried food pieces from the fryer, wherein a second conveyor deposits the fried food pieces onto the adjustable draining device, and wherein the second conveyor conveys the fried food pieces at a higher velocity than the first conveyor;

wherein the controlled environment comprises at least one of a temperature, oxygen content, or steam content;

wherein the enclosure further comprises a set of flow-control outlets;

wherein the set of flow-control outlets is a plurality of exhaust stacks, wherein each of the plurality of exhaust stacks is positioned at a different location along a length of the fryer system;

wherein each of the exhaust stacks comprises an adjustable damper to control a release of steam from one or more of the different locations along the length of the fryer system;

wherein each of the adjustable dampers can assume a completely open configuration, a partially open configuration, and a completely closed configuration;

wherein the fryer system further comprises an environmental control subsystem comprising a set of feed lines in fluid communication with a return line, wherein each of the set of feed lines originates at a different location along a length of the fryer system, and wherein the return line terminates at the draining region;

wherein environmental control subsystem further comprises a heat exchanger, wherein the heat exchanger re-heats steam drawn from one or more of the set of feed lines to form re-heated steam, and wherein the re-heated steam is introduced into the draining region;

wherein the environmental control subsystem further comprises an inert gas dispenser, wherein the inert gas dispenser is positioned to introduce an inert gas into the draining region;

wherein the environmental control subsystem further comprises at least one of a blower and a fan;

wherein the fryer system further comprises an oil content sensor downstream from the draining region, wherein the oil content sensor provides oil content data for adjusting fryer system variables that control at least one of the residence time of the fried food pieces in the draining region, a temperature of the draining region, a steam concentration in the draining region, an oxygen concentration in the draining region, and a temperature of added oil in the fryer;

wherein the fryer system further comprises an oil weir, wherein the oil weir provides the added oil;

wherein the adjustable draining device comprises a first draining belt that conveys fried food pieces in a first direction, and wherein the adjustable draining device comprises a second draining belt positioned beneath the first draining belt and configured to receive the fried food pieces from the first draining belt, and wherein the second draining belt conveys the fried food pieces in a second direction different from the first direction;

wherein at least a portion of the enclosure can be opened to purge the controlled environment from the draining region.

In a second embodiment, novel aspects of the present disclosure are directed to a method for producing fried food pieces in a fryer system, the method comprising: frying a plurality of food pieces in hot oil to form the fried food pieces; transferring the fried food pieces to an adjustable draining device located within a draining region of the fryer system; maintaining a controlled environment in the draining region; and conveying the fried food pieces through the draining region for a residence time.

In another aspect of the second embodiment, novel aspects of the present disclosure are directed to a method for producing fried food pieces in a fryer system, the method comprising: frying a plurality of food pieces in hot oil to form the fried food pieces; transferring the fried food pieces to an adjustable draining device located within a draining region of the fryer system; maintaining a controlled environment in the draining region; and conveying the fried food pieces through the draining region for a residence time; and one or limitation selected from the following:

introducing added oil to the hot oil, wherein the added oil is provided by an oil weir;

reducing a bed depth of the fried food pieces before depositing the fried food pieces on the adjustable draining device;

wherein the bed depth of the fried food pieces is reduced to a monolayer;

transferring the fried food pieces from a first conveyor of a set of takeout conveyors to a second conveyor of the set of takeout conveyors, and wherein the second conveyor conveys the fried food pieces at a higher velocity than the first conveyor;

generating fresh steam; and introducing the fresh steam into the draining region;

conveying steam generated in the frying step from a frying region of the fryer system to the draining region;

selectively releasing the steam from one or more of a set of flow-control outlets;

re-heating at least a portion of the steam to form re-heated steam; and introducing the re-heated steam into the draining region;

injecting an inert gas into a draining region;

adjusting a temperature of the inert gas;

adjusting fryer system variables to achieve the controlled environment having a steam composition of at least 80% steam, an oxygen concentration of less than 10%, and a temperature between 105-180° C.;

orienting the fried food pieces in a substantially vertical orientation on the adjustable draining device; and analyzing an oil content of the fried food pieces downstream from the adjustable draining device; and adjusting fryer system variables based on the oil content of the fried food pieces.

I claim:

1. A fryer system comprising:
   a fryer in a frying region of the fryer system, wherein the fryer produces fried food pieces;
   an adjustable draining device in a draining region of the fryer system, wherein the draining region is downstream from the frying region, and wherein the adjustable draining device controls a residence time of the fried food pieces in the draining region;
   a set of takeout conveyors bridging the frying region and the draining region, wherein the set of takeout conveyors reduces a bed depth of the fried food pieces as the set of takeout conveyors transfers the fried food pieces from the fryer to the adjustable draining device, wherein the adjustable draining device is a set of inclined conveyor belts;
   an enclosure at least partially enclosing the frying region and the draining region, wherein the enclosure maintains a controlled environment within the draining region; and
   an environmental control subsystem comprising a plurality of feed lines in fluid communication with a return line, wherein each of the plurality of feed lines originates at a different location along a length of the fryer system, wherein the return line terminates at the draining region, wherein steam is recovered from any one of the plurality of feed lines based on a desired temperature of the draining region.

2. The fryer system of claim 1, wherein the adjustable draining device is a vertical orientation device that orients the fried food pieces in at least a generally vertical orientation.

3. The fryer system of claim 2, wherein each of the set of inclined conveyor belts comprises a plurality of vertical orientation members extending outwardly from a conveying surface, and wherein the plurality of vertical orientation members span a width of the conveyor.

4. The fryer system of claim 3, wherein the adjustable draining device comprises at least one of a variable velocity, a variable elevation, and a variable number of conveyor belts in the set of conveyor belts.

5. The fryer system of claim 1, wherein the set of takeout conveyors comprises a plurality of conveyor belts arranged in series, and wherein the set of takeout conveyors reduces the bed depth of the fried food pieces to a substantially monolayered state.

6. The fryer system of claim 1, wherein the set of takeout conveyors comprises at least two conveyors arranged in series, wherein a first conveyor removes fried food pieces from the fryer, wherein a second conveyor deposits the fried food pieces onto the adjustable draining device, and wherein the second conveyor conveys the fried food pieces at a higher velocity than the first conveyor.

7. The fryer system of claim 1, wherein the enclosure further comprises a set of flow-control outlets.

8. The fryer system of claim 7, wherein the set of flow-control outlets is a plurality of exhaust stacks, wherein each of the plurality of exhaust stacks is positioned at a different location along a length of the fryer system.

9. The fryer system of claim 1, wherein the environmental control subsystem further comprises a heat exchanger, wherein the heat exchanger heats exhaust drawn from one or more of the set of feed lines.

10. The fryer system of claim 1, wherein the environmental control subsystem further comprises an inert gas dispenser, wherein the inert gas dispenser is positioned to introduce an inert gas into the draining region.

11. The fryer system of claim 1, further comprising:
an oil content sensor downstream from the draining region, wherein the oil content sensor provides oil content data for adjusting system variables.

12. A method for producing fried food pieces in a fryer system, the method comprising:
frying a plurality of food pieces in hot oil to form the fried food pieces;
transferring the fried food pieces from the hot oil onto an adjustable draining device located within a draining region of the fryer system, wherein the adjustable draining device is a set of inclined conveyor belts;
maintaining a controlled environment in the draining region by conveying exhaust generated by the fryer system to an upstream position of the draining region, wherein the exhaust is selectively released from any one of a plurality of flow-control outlets based on a desired temperature of the draining region, wherein each of the plurality of flow-control outlets are positioned at a different location along a length of the fryer system; and
conveying the fried food pieces through the draining region for a residence time.

13. The method of claim 12, wherein the transferring step further comprises:
reducing a bed depth of the fried food pieces before depositing the fried food pieces on the adjustable draining device.

14. The method of claim 13, wherein the step of reducing the bed depth further comprises:
transferring the fried food pieces from a first conveyor of a set of takeout conveyors to a second conveyor of the set of takeout conveyors, and wherein the second conveyor conveys the fried food pieces at a higher velocity than the first conveyor.

15. The method of claim 12, further comprising:
heating at least a portion of the exhaust to form heated exhaust; and
introducing the heated exhaust into the draining region.

16. The method of claim 12, further comprising:
orienting the fried food pieces in a substantially vertical orientation on the adjustable draining device.

17. The method of claim 12, further comprising:
analyzing an oil content of the fried food pieces downstream from the adjustable draining device; and
adjusting system variables based on the oil content of the fried food pieces.

18. A fryer system comprising:
a fryer in a frying region of the fryer system, wherein the fryer produces fried food pieces;
an adjustable draining device in a draining region of the fryer system, wherein the draining region is downstream from the frying region, and wherein the adjustable draining device controls a residence time of the fried food pieces in the draining region;
a set of takeout conveyors bridging the frying region and the draining region, wherein the set of takeout conveyors reduces a bed depth of the fried food pieces as the set of takeout conveyors transfers the fried food pieces from the fryer to the adjustable draining device, wherein the adjustable draining device is a set of inclined conveyor belts;
an enclosure at least partially enclosing the frying region and the draining region, wherein the enclosure maintains a controlled environment within the draining region; and
an environmental control subsystem comprising a plurality of feed lines in fluid communication with a return line, wherein the return line terminates at the draining region, wherein each of the plurality of feed lines originates at a different location along a length of the fryer system, wherein at least one of the plurality of feed lines originates downstream of the return line.

19. The method of claim 12, wherein at least one of the plurality of flow-control outlets is positioned downstream of the draining region.

* * * * *